United States Patent
Bian et al.

(10) Patent No.: US 9,814,816 B2
(45) Date of Patent: *Nov. 14, 2017

(54) ARTIFICIAL VENTRICLES

(71) Applicant: Corvivo, Inc., Richmond (CA)

(72) Inventors: Xiaoming Bian, Dalian (CN); Frank Zheng, Kirkland, WA (US)

(73) Assignee: Corvivo, Inc., Coquitlam, British Columbia (CA)

(*) Notice: Subject to any disclaimer, the term of this patent is extended or adjusted under 35 U.S.C. 154(b) by 0 days.

This patent is subject to a terminal disclaimer.

(21) Appl. No.: 14/900,613

(22) PCT Filed: Jun. 23, 2014

(86) PCT No.: PCT/CA2014/050598
§ 371 (c)(1),
(2) Date: Dec. 21, 2015

(87) PCT Pub. No.: WO2014/201575
PCT Pub. Date: Dec. 24, 2014

(65) Prior Publication Data
US 2016/0310652 A1    Oct. 27, 2016

Related U.S. Application Data

(63) Continuation-in-part of application No. 13/924,472, filed on Jun. 21, 2013, now Pat. No. 9,320,841.

(51) Int. Cl.
*A61M 1/12* (2006.01)
*A61M 1/10* (2006.01)

(52) U.S. Cl.
CPC .......... *A61M 1/122* (2014.02); *A61M 1/1055* (2014.02); *A61M 1/1067* (2013.01);
(Continued)

(58) Field of Classification Search
CPC .............. A61M 1/1037; A61M 1/1043; A61M 1/1046; A61M 1/1055; A61M 1/1086
(Continued)

(56) References Cited

U.S. PATENT DOCUMENTS 3,768,931 A    10/1973  Willis, Jr.
4,185,617 A     1/1980  Hutchins
(Continued)

FOREIGN PATENT DOCUMENTS

EP    1486217 A1    12/2004
EP    2371405 A1    10/2011
(Continued)

OTHER PUBLICATIONS

WIPO, Canada International Search Authority, International Search Report and Written Opinion dated Nov. 24, 2014 in International Patent Application No. PCT/CA2014/050598, 9 pages.

*Primary Examiner* — Allen Porter, Jr.
(74) *Attorney, Agent, or Firm* — Inskeep IP Group, Inc.

(57) ABSTRACT

A artificial ventricle comprises an inlet for receiving blood, an outlet for discharging blood, and a chamber disposed between the inlet and the outlet. There is also a mechanism for actuating the artificial ventricle between an expanded configuration and a contracted configuration. In the expanded configuration, blood flows into the inlet. In the contracted configuration, blood flows out of the outlet. There may be a one-way valve at the outlet for preventing blood flow back into the chamber. The one-way valve may be a diaphragm valve. The chamber may have a resilient outer wall. The chamber may have an ovoid shape.

8 Claims, 11 Drawing Sheets

(52) U.S. Cl.
CPC ........ *A61M 1/1086* (2013.01); *A61M 1/1087* (2014.02); *A61M 1/1098* (2014.02); *A61M 1/125* (2014.02); *A61M 2230/005* (2013.01); *A61M 2230/04* (2013.01)

(58) Field of Classification Search
USPC .................................. 600/16–18; 623/3, 11
See application file for complete search history.

(56) References Cited

U.S. PATENT DOCUMENTS

| | | |
|---|---|---|
| 4,621,617 A | 11/1986 | Sharma |
| 5,332,403 A | 7/1994 | Kolff |
| 6,123,724 A | 9/2000 | Denker |
| 6,251,061 B1 | 6/2001 | Hastings et al. |
| 6,264,601 B1 | 7/2001 | Jassawalla et al. |
| 7,273,446 B2 | 9/2007 | Spence |
| 7,357,771 B2 | 4/2008 | Peters et al. |
| 7,402,134 B2 | 7/2008 | Moaddeb et al. |
| 8,303,481 B2 | 11/2012 | Kassab et al. |
| 8,382,651 B2 | 2/2013 | Kassab et al. |
| 2002/0151761 A1 | 10/2002 | Viole et al. |
| 2004/0116769 A1 | 6/2004 | Jassawalla et al. |
| 2009/0099498 A1 | 4/2009 | Demers et al. |
| 2009/0292160 A1 | 11/2009 | Nieman |

FOREIGN PATENT DOCUMENTS

| | | |
|---|---|---|
| WO | WO9604945 A1 | 2/1996 |
| WO | WO02085432 A1 | 10/2002 |
| WO | WO2004045677 A1 | 6/2004 |
| WO | WO2004045677 A2 | 6/2004 |
| WO | WO 2007/087014 A2 | 8/2007 |
| WO | WO2014201575 A1 | 12/2014 |

ARTIFICIAL VENTRICLES

RELATED APPLICATIONS

This application is the U.S. National Phase of and claims priority to International Patent Application No. PCT/CA2014/050598, International Filing Date Jun. 23, 2014, entitled Artificial Ventricles; which is a continuation-in-part of U.S. application Ser. No. 13/924,472 filed Jun. 21, 2013 entitled Ventricular Assist Device (now U.S. Pat. No. 9,320,841 issued Apr. 26, 2016); both of which are incorporated herein by reference in their entireties.

BACKGROUND OF THE INVENTION

Field of the Invention
Description of the Related Art
It is known to use intra-aortic balloon pumps, operating in counterpulsation, to assist heart function. However, intra-aortic balloon pumps may be insufficient to sustain hemodynamics if the left heart is severely injured. There have accordingly been a number of alternative devices developed for assisting heart function in patients with chronic heart failure. For example, U.S. Pat. No. 7,347,811 which issued on Mar. 25, 2008 to Peters et al., and the full disclosure of which is incorporated herein by reference, discloses a device for providing counter-pulsation heart assist by deforming the aorta. In a preferred embodiment, the deformation pressure is applied cyclically, preferably in synchrony with the diastolic period of the heart. The deformation pressure may be applied to the outer wall of the aorta or to a patch covering a resected opening in the wall of the aorta. There however remains a need for improved ventricular assist devices.

SUMMARY OF THE INVENTION

It is an object of the present invention to provide an artificial ventricle and a method of artificial ventricle assist.

There is provided an artificial ventricle comprising an inlet for receiving blood, an outlet for discharging blood, and a chamber disposed between the inlet and the outlet. There is also a mechanism for actuating the artificial ventricle between an expanded configuration and a contracted configuration. In the expanded configuration blood flows into the inlet. In the contracted configuration blood flows out of the outlet. There may be a one-way valve at the outlet for preventing blood flow back into the chamber. The one-way valve may be a diaphragm valve. The chamber may have a resilient outer wall. The chamber may have an ovoid shape.

The mechanism for actuating the artificial ventricle between the expanded configuration and the contracted configuration may include a first pad disposed on the resilient outer wall of the chamber and a second pad disposed on the resilient outer wall of the chamber opposite of the first pad. The first pad may have a magnetic field generator and the second pad may have a material which is attracted to the magnetic field generator when the magnetic field generator generates a magnetic field. The second pad may move towards the first pad when the magnetic field generator generates a magnetic field, and thereby actuate the artificial ventricle to the contracted configuration by contracting the resilient outer wall of the chamber. The resilient outer wall of the chamber may actuate the artificial ventricle to the expanded configuration when the magnetic field generator is not generating a magnetic field and the material is not attracted to the magnetic field generator.

The mechanism for actuating the artificial ventricle between the expanded configuration and the contracted configuration may alternatively include a magnetic field generator integral with the resilient outer wall of the chamber and a material integral with the resilient outer wall of the chamber which is attracted to the magnetic field generator when the magnetic field generator generates a magnetic field. The material may move toward the magnetic field generator when the magnetic field generator generates a magnetic field and thereby actuate the artificial ventricle to the contracted configuration by contracting the resilient outer wall of the chamber. The resilient outer wall of the chamber may actuate the artificial ventricle to the expanded configuration when the magnetic field generator is not generating a magnetic field and the material is not attracted to the magnetic field generator.

The artificial ventricle may further include an electrical energy supply electrically connected to the magnetic field generator, a controller which drives the electric energy supply to either energize or de-energize the magnetic field generator, and an ECG signal generator which signals the controller when there is ventricular diastole and ventricular systole. The controller may drive the electrical energy supply to energize the magnetic field generator when the ECG signal generator signals the controller that there is ventricular diastole. The controller may drive the electrical energy supply to de-energize the magnetic field generator when the ECG signal generator signals the controller that there is ventricular systole.

There is also provided a method of left ventricle assist comprising removing a portion of the aorta distal of the native aortic valve and implanting an artificial ventricle to replace the removed portion of the aorta. The artificial ventricle comprises an inlet for receiving blood, an outlet for discharging blood, and a chamber disposed between the inlet and the outlet. There is also a mechanism for actuating the artificial ventricle between an expanded configuration and a contracted configuration. In the expanded configuration blood flows into the inlet. In the contracted configuration blood flows out of the outlet. The artificial ventricle is actuated to the expanded configuration during ventricular systole and the artificial ventricle is actuated to the contracted configuration during ventricular diastole.

There is further provided a method of right ventricle assist comprising removing a portion of the pulmonary artery distal of the native pulmonic valve and implanting an artificial ventricle to replace the removed portion of the pulmonary artery. The artificial ventricle comprises an inlet for receiving blood, an outlet for discharging blood, and a chamber disposed between the inlet and the outlet. There is also a mechanism for actuating the artificial ventricle between an expanded configuration and a contracted configuration. In the expanded configuration blood flows into the inlet. In the contracted configuration blood flows out of the outlet. The artificial ventricle is actuated to the expanded configuration during ventricular systole and the artificial ventricle is actuated to the contracted configuration during ventricular diastole.

BRIEF DESCRIPTIONS OF DRAWINGS

The invention will be more readily understood from the following description of the embodiments thereof given, by way of example only, with reference to the accompanying drawings, in which.

DESCRIPTIONS OF THE PREFERRED EMBODIMENTS

Figure 1:
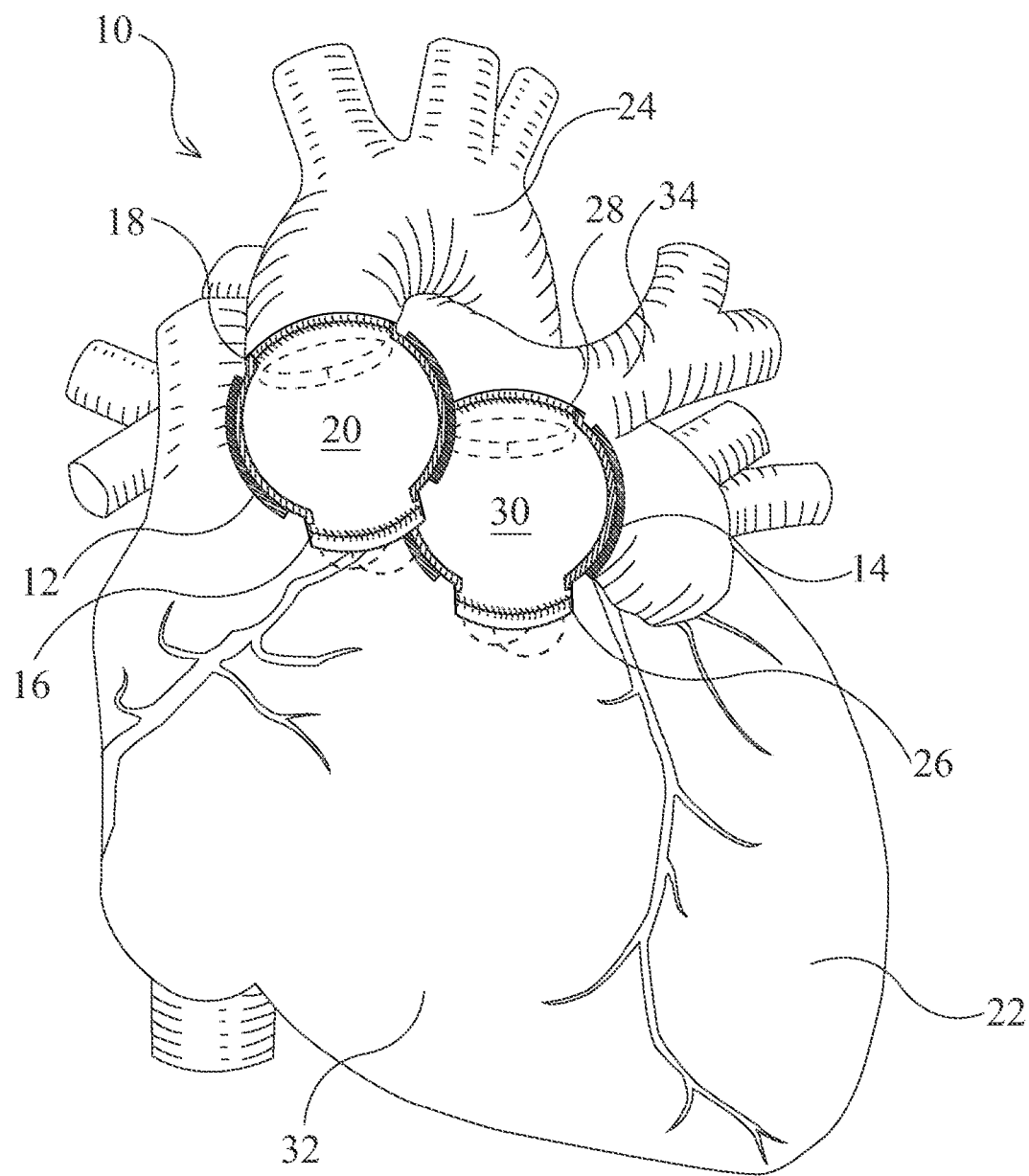
FIG. 1 is a fragmentary, sectional view of a biventricular failed heart provided with an implanted left artificial ventricle and an implanted right artificial ventricle.

Referring to the drawings and first to FIG. 1, there is shown a biventricular failed heart 10 provided with an implanted left artificial ventricle 12 and an implanted right artificial ventricle 14. The left artificial ventricle 12 generally comprises an inlet 16, an outlet 18, and a chamber 20 disposed between the inlet 16 and the outlet 18. The inlet 16 of the left artificial ventricle 12 is in fluid communication with a failed left ventricle 22 of the heart 10 and the outlet 18 of the left artificial ventricle is surgically connected to and in fluid communication with the aorta 24. The left artificial ventricle 12 accordingly assists blood flow from the left ventricle 22 to the aorta 24. More specifically, a portion of the aorta 24 distal of the native aortic valve (not shown) is removed and replaced by the left artificial ventricle 12. The inlet 16 of the left artificial ventricle 12 is connected to a proximal open end of the aorta 24. The outlet 18 of the left artificial ventricle 12 is connected to a distal open end of the aorta 24. The failed left ventricle 22 functions as a pathway for blood flow from the left atrium to the aorta 24 as well as a blood reservoir as will be described below.

Likewise the right artificial ventricle 14 generally comprises an inlet 26, an outlet 28, and a chamber 30 disposed between the inlet 26 and the outlet 28. The inlet 26 of the right artificial ventricle 14 is in fluid communication with a failed right ventricle 32 of the heart 10 and the outlet 28 of the left artificial ventricle is surgically connected to and in fluid communication with the pulmonary artery 34. The right artificial ventricle 14 accordingly allows for blood flow from the right ventricle 32 to the pulmonary artery 34. More specifically, a portion of the pulmonary artery 34 distal of the native pulmonic valve (not shown) is removed and replaced by the right artificial ventricle 14. The inlet 26 of the right artificial ventricle 14 is surgically connected to a proximal open end of the pulmonary artery 34. The outlet 28 of the right artificial ventricle 14 is connected to a distal open end of the pulmonary artery 34. The failed right ventricle 32 functions as a pathway for blood flow from the right atrium to the pulmonary artery 34 as well as a blood reservoir as will be described below.

Figure 2:
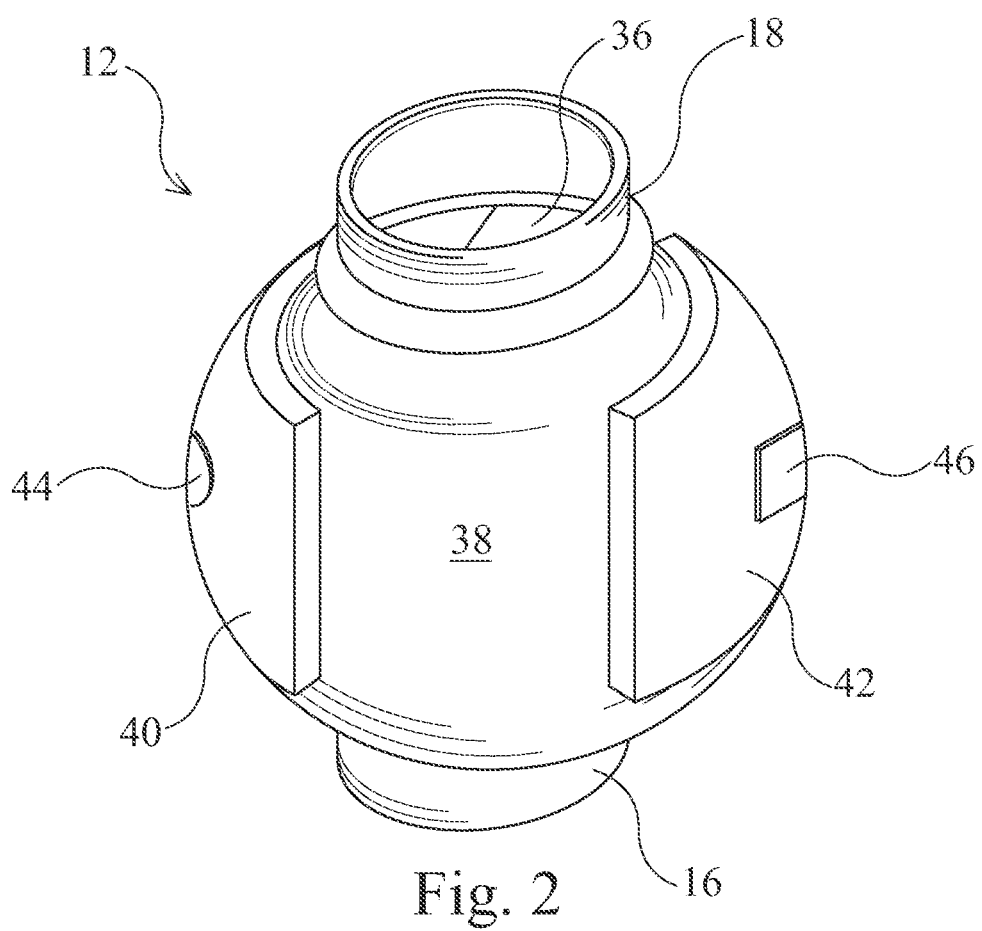
FIG. 2 is a perspective view of the left artificial ventricle of FIG. 1.

The left artificial ventricle 12 and the right artificial ventricle 14 have a substantially identical structure and function in a substantially identical manner. Accordingly, only the left artificial ventricle 12 is described in detail herein with the understanding that the right artificial ventricle 14 has a substantially identical structure and functions in a substantially identical manner. The left artificial ventricle 12 is shown in greater detail in FIG. 2 and is provided with a one-way valve 36 at the outlet 18 thereof. The one-way valve 36 is a diaphragm check valve in this example but any suitable one-way valve may be used. There is a resilient outer wall 38 which defines the chamber 20 of the left artificial ventricle 12. The resilient outer wall 38 and therefore the left artificial ventricle 12 are substantially ovoid in this example as this shape may prevent thrombosis formation. However, in other examples, the left artificial ventricle 12 may have any suitable geometry.

There are flexible pads 40 and 42 on opposite sides of the resilient outer wall 38. In this example, the pads 40 and 42 are symmetrical in shape but one of the pads 40 is provided with a magnetic field generator in the form of an electromagnet 44 while the other one of the pads 42 is provided with a material 46 which will be attracted to the electromagnet 44 when the electromagnet 44 generates a magnetic field. The material 46 is a metal in this example. However, in other examples the material may be a magnetic field generator that generates a magnetic field having a polarity opposite to the magnetic field generated by the electromagnet 44. The electromagnet 44 and the material 46 may be disposed on or within their respective flexible pads 40 and 42. Alternatively, a magnetic field generator and a material which will be attracted to the magnetic field generator when the magnetic field generator generates a magnetic field may both be integral with the walls of the outer wall of the chamber.

Figure 3:
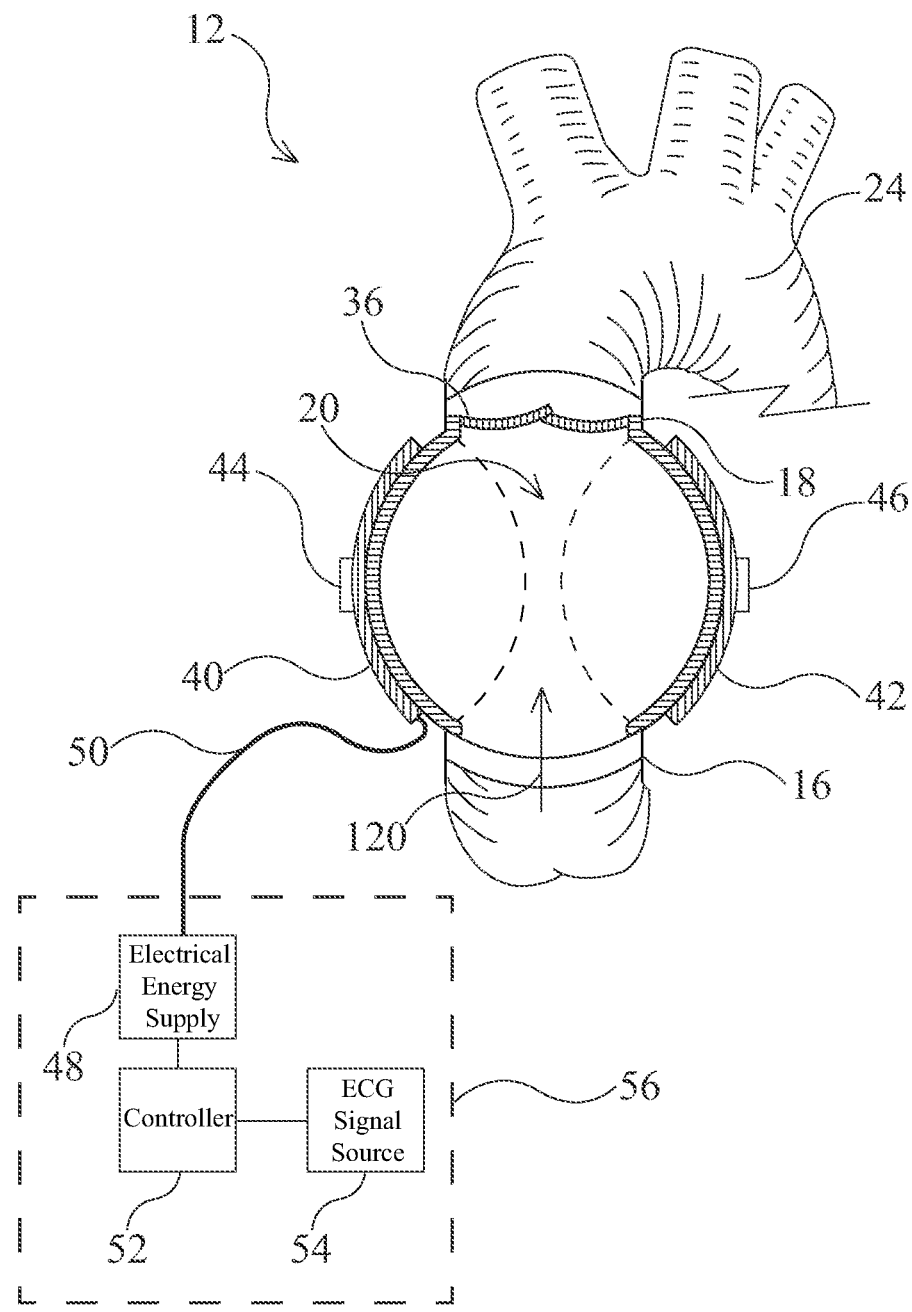
FIG. 3 is a sectional view of the left artificial ventricle of FIG. 1 in an expanded configuration.
Figure 4:
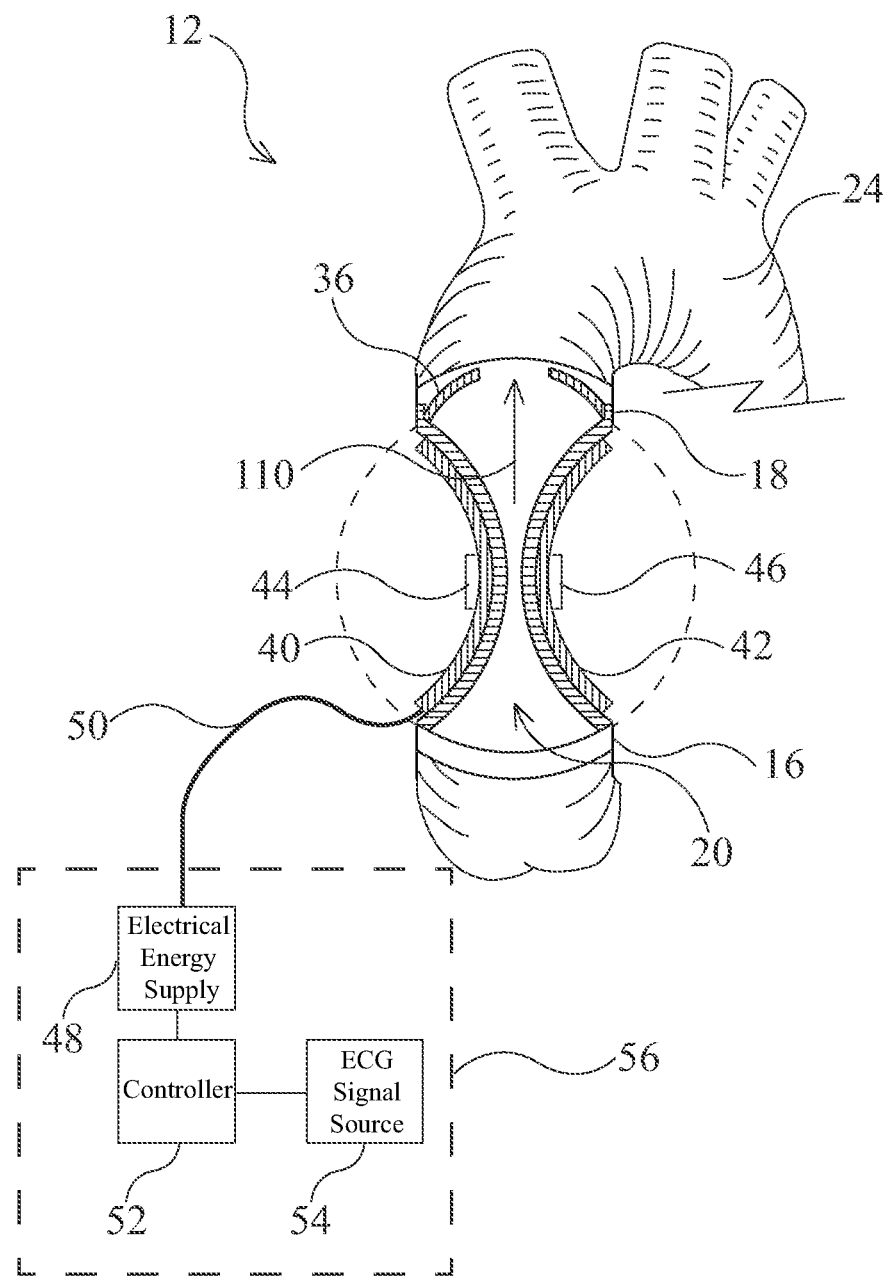
FIG. 4 is a sectional view of the left artificial ventricle of FIG. 1 in a contracted configuration.
Figure 5:
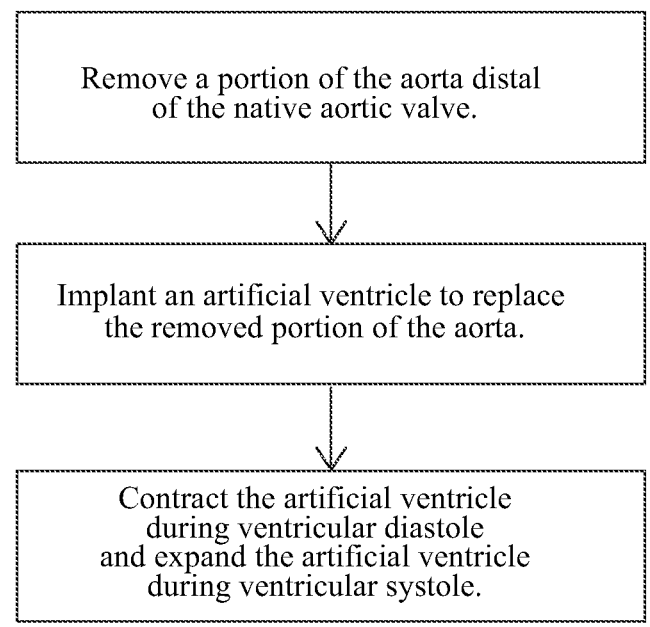
FIG. 5 is a flowchart showing a method for providing left ventricle assist.
Figure 6:
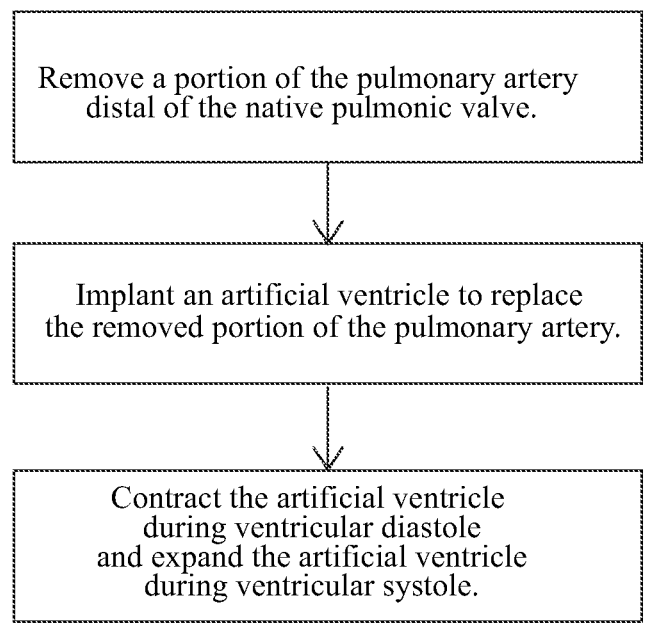
FIG. 6 is a flowchart showing a method for providing right ventricle assist.
Figure 7:
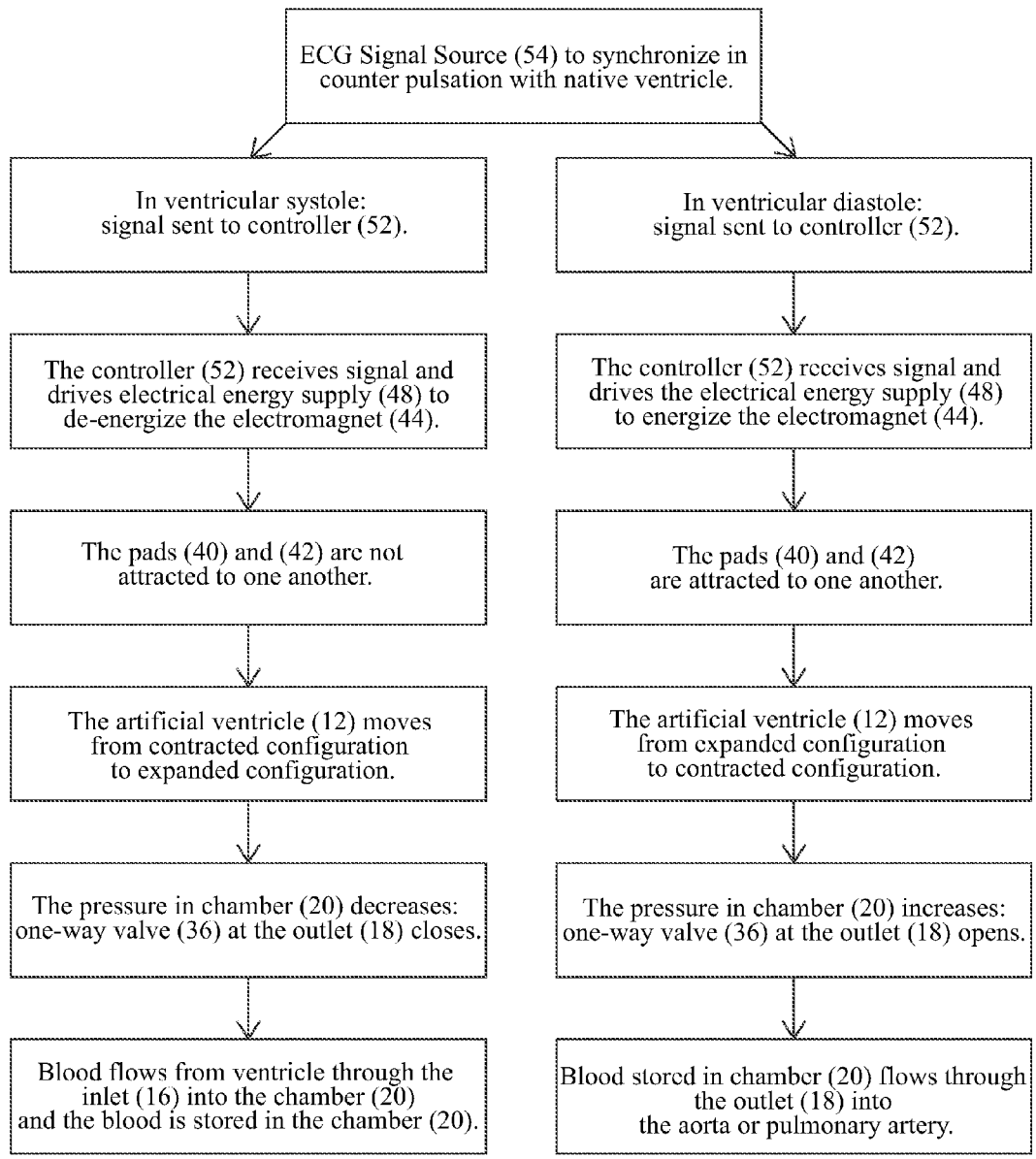
FIG. 7 is a flowchart showing operation of the artificial ventricles of FIG. 1.

Referring now to FIGS. 3 and 4, operation of the left artificial ventricle 12 is shown. In FIG. 3 the left artificial ventricle 12 is shown in an expanded configuration. In FIG. 4 the left artificial ventricle 12 is shown in a contracted configuration. An electrical energy supply 48, for example a battery, is electrically connected with the electromagnet 44 via an electrical conductor which, in this example, is a wire 50. The electrical energy supply 48 is driven by a controller 52 which receives signals from an ECG signal source 54. The controller 52 drives the electrical energy supply 48 to energize the electromagnet 44 when the ECG signal source 54 signals that there is ventricular diastole and the controller 52 drives the electrical energy supply 48 to de-energize the electromagnet 44 when the ECG signal source 54 signals that there is ventricular systole. The electrical energy supply 48, the controller 52, and the ECG signal source 54 may all be part of an implanted pacemaker type device 56.

The left artificial ventricle 12 moves from the expanded configuration to the contracted configuration when the electromagnet 44 is energized. This is because the electromagnet 44 and the material 46 in the respective flexible pads 40 and 42 are then drawn towards one another. The pressure differential when the left artificial ventricle 12 is in the contracted configuration opens the one-way valve 36 and blood in the chamber 20 flows into the aorta 24 through the outlet 18 as indicated generally by arrow 110 in FIG. 4. The left artificial ventricle 12 moves from the contracted configuration to the expanded configuration when the electromagnet 44 is de-energized. This is because the electromagnet 44 and the material 46 in the respective flexible pads 40 and 42 are no longer attracted to one another and the resilient nature of the resilient outer wall 38 actuates the left artificial ventricle 12 to move to the expanded configuration. The pressure differential when the left artificial ventricle 12 is in the expanded configuration closes the one-way valve 36. Accordingly, blood which flows into the chamber 20 through the inlet 16, as indicated generally by arrow 120 in FIG. 3, is stored in the chamber and the chamber temporarily functions as a blood reservoir.

In operation, a portion of the ascending aorta is surgically removed and the left artificial ventricle 12 is implanted to replace the removed portion of the aorta. The two pads 40 and 42 are disposed on the resilient outer wall 38 of the chamber 20 on opposite sides of the resilient outer wall 38. One of the pads 40 is provided with the electromagnet 44 while the other one of the pads 42 is provided with the material 46 which is attracted to the electromagnet 44 when the electromagnet 44 generates a magnetic field. The electromagnet 44 is connected to the implanted pacemaker type device 56 through the wire 50. The implanted pacemaker type device 56 senses the patient's ECG and energizes and de-energizes the electromagnet 44 based on the patient's ECG. The electromagnet 44 is de-energized and the artificial ventricle 12 moves from the contracted configuration to the expanded configuration when the failed left ventricle 22 contracts as indicated by an R wave of the ECG. The one-way valve 36 at the outlet 18 simultaneously closes and the pressure inside the chamber 20 decreases while the aortic valve opens. The result is blood flow from the failed left ventricle 22 through the inlet 16 and into the chamber 20 of the left artificial ventricle 12. The electromagnet 44 is then energized and the artificial ventricle 12 moves from the expanded configuration to the contracted configuration when the failed left ventricle 22 relaxes as indicated by a T wave of the ECG. The one-way valve 36 at the outlet 18 simultaneously opens so the blood stored in the chamber 20 flows into the aorta 24. The left ventricle may accordingly function merely as a pathway for blood flowing from the left atrium to the left artificial ventricle 12 while the left artificial ventricle 12 functions as a pump.

The right artificial ventricle 14 functions in a substantially similar manner with the exception that a portion of the pulmonary trunk is surgically removed and the right artificial ventricle 14 is implanted to replace the removed portion of the pulmonary trunk. The right ventricle may then merely function as a pathway for blood flowing from the right atrium to the right artificial ventricle 14 while the right artificial ventricle 14 functions as a pump.

Figure 8:
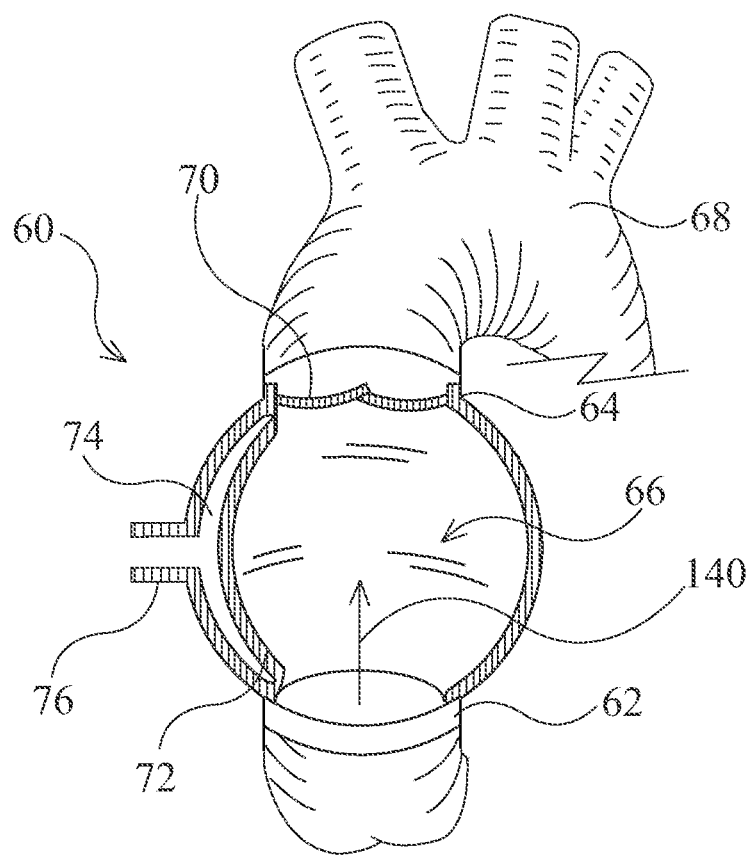
FIG. 8 is a sectional view of another artificial ventricle in an expanded configuration.
Figure 9:
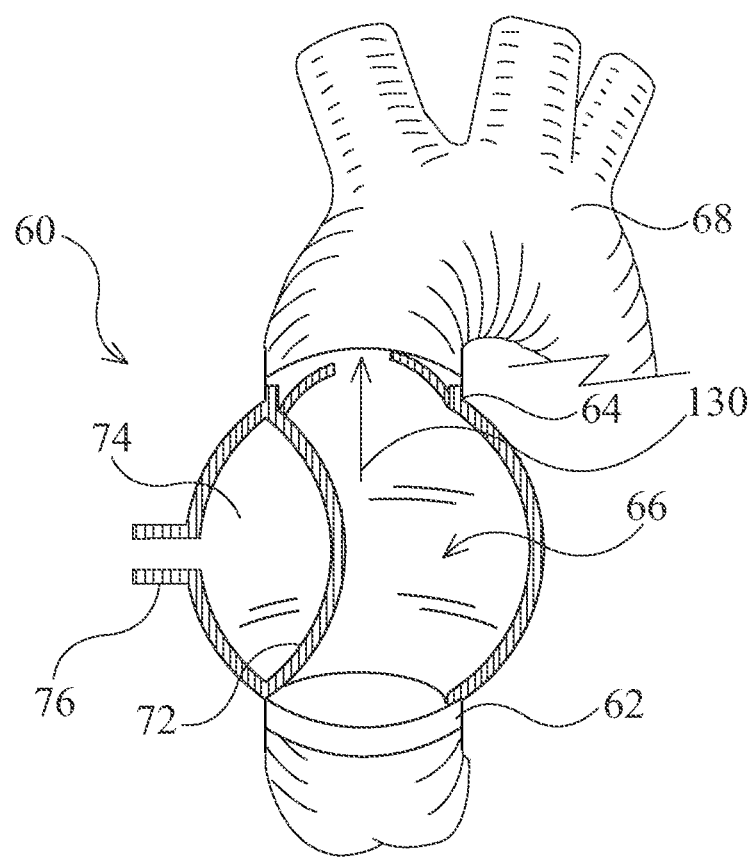
FIG. 9 is a sectional view of the artificial ventricle of FIG. 8 in a contracted configuration.

In the example shown in FIGS. 1 to 7, the mechanism for actuating the artificial ventricle between the expanded configuration and the contracted configuration is an electromagnetic mechanism. However, in other examples other mechanisms such as mechanical mechanisms, hydraulic mechanisms, electrical mechanisms, etc. may be used to actuate the artificial ventricle between the expanded configuration and the contracted configuration. For example, FIGS. 8 and 9 show another artificial ventricle 60 implanted in a failed left ventricle (not shown). The artificial ventricle 60 generally comprises an inlet 62, an outlet 64, and a main chamber 66 disposed between the inlet 62 and the outlet 64. The inlet 62 of the artificial ventricle 60 is in fluid communication with the failed left ventricle and the outlet 64 of the artificial ventricle 60 is in fluid communication with the aorta 68. There is a one-way valve 70 at the outlet 64 of the artificial ventricle 60. A resilient member 72 separates the main chamber 66 from an expansion chamber 74 which is in fluid communication with a fluid source via a conduit 76.

The artificial ventricle 60 may be actuated from an expanded configuration, shown in FIG. 8, and a contracted configuration, shown in FIG. 9, by introducing fluid into the expansion chamber 74. The artificial ventricle 60 may be actuated from the contracted configuration to the expanded configuration by withdrawing fluid from the expansion chamber 74. The pressure differential when the artificial ventricle 60 is in the contracted configuration opens the one-way valve 70 and blood in the main chamber 66 flows into the aorta 68 through the outlet 64 as indicated generally by arrow 130 in FIG. 9. The pressure differential when the artificial ventricle 60 is in the expanded configuration closes the one-way valve 70. Accordingly, blood which flows into the chamber 20 through the inlet 62, as indicated generally by arrow 140 in FIG. 8, is stored in the chamber and the chamber temporarily functions as a blood reservoir.

Figure 10:
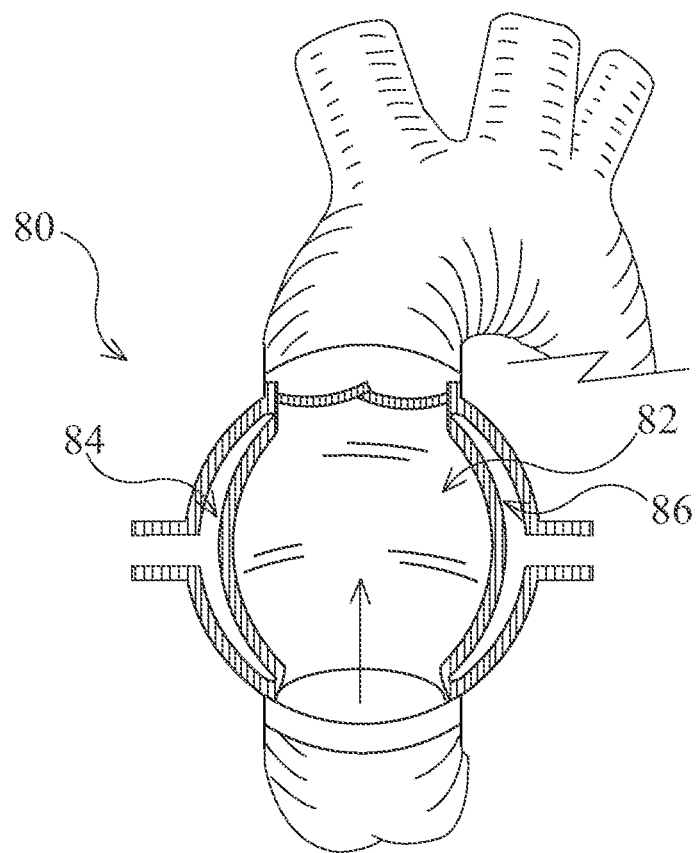
FIG. 10 is a sectional view of another artificial ventricle in an expanded configuration.
Figure 11:
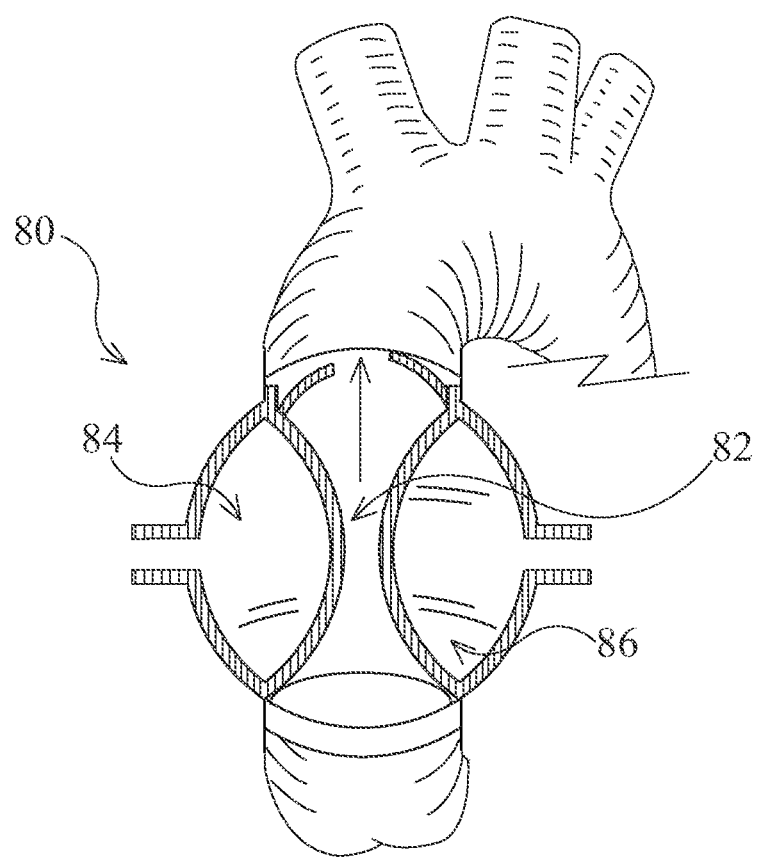
FIG. 11 is a sectional view of the artificial ventricle of FIG. 10 in a contracted configuration.

FIGS. 10 and 11 show yet another artificial ventricle 80 which is generally similar to the artificial ventricle 60 shown in FIGS. 8 and 9 with the exception that the main chamber 82 is disposed between expansion chambers 84 and 86.

The artificial ventricles disclosed herein may be fully implanted and replace the function of a late stage or fully failed ventricle. Blood volume per stroke may be designed into the shape and contraction means to achieve normal ventricle performance levels. Blood volume per stroke may be independent of ventricle performance. Providing the artificial ventricle with a one-way or back-flow prevention valve may improve efficiency by preventing blood flow back into the chamber.

It will be understood by a person skilled in the art that many of the details provided above are by way of example only, and are not intended to limit the scope of the invention which is to be determined with reference to the following claims.

The invention claimed is:
1. An artificial ventricle comprising:
an inlet for receiving blood;
an outlet for discharging blood;
a chamber disposed between the inlet and the outlet; and
an actuation device having an energized state activating an electromagnet or a fluid pump, that causes movement of the artificial ventricle between an expanded configuration and a contracted configuration, wherein in the expanded configuration blood flows into the inlet and in the contracted configuration blood flows out of the outlet;
wherein the chamber has a resilient outer wall and the actuation device includes:
a first pad disposed on the resilient outer wall of the chamber, the first pad having a magnetic field generator; and
a second pad disposed on the resilient outer wall of the chamber opposite of the first pad, the second pad having a material which is attracted to the magnetic field generator when the magnetic field generator generates a magnetic field, wherein the second pad moves towards the first pad when the magnetic field generator generates a magnetic field and thereby actuates the artificial ventricle to the contracted configuration by contracting the resilient outer wall of the chamber, and wherein the resilient outer wall of the chamber actuates the artificial ventricle to the expanded configuration when the magnetic field generator is not generating a magnetic field and the material is not attracted to the magnetic field generator.

2. An artificial ventricle comprising:
an inlet for receiving blood;
an outlet for discharging blood;
a chamber disposed between the inlet and the outlet;
an actuation device having an energized state activating an electromagnet or a fluid pump, that causes movement of the artificial ventricle between an expanded configuration and a contracted configuration, wherein in the expanded configuration blood flows into the inlet and in the contracted configuration blood flows out of the outlet; and
a one-way valve at the outlet for preventing blood flow back into the chamber;
wherein the chamber has a resilient outer wall and the actuation device includes:
a first pad disposed on the resilient outer wall of the chamber, the first pad having a magnetic field generator; and
a second pad disposed on the resilient outer wall of the chamber opposite of the first pad, the second pad having a material which is attracted to the magnetic field generator when the magnetic field generator generates a magnetic field, wherein the second pad moves towards the first pad when the magnetic field generator generates a magnetic field and thereby actuates the artificial ventricle to the contracted configuration by contracting the resilient outer wall of the chamber, and wherein the resilient outer wall of the chamber actuates the artificial ventricle to the expanded configuration when the magnetic field generator is not generating a magnetic field and the material is not attracted to the magnetic field generator.

3. The artificial ventricle as claimed in claim 2 wherein the one-way valve is a diaphragm valve.

4. The artificial ventricle as claimed in claim 1 wherein the chamber has an ovoid shape.

5. The artificial ventricle as claimed in claim 1 further including:
an electrical energy supply electrically connected to the magnetic field generator;
a controller which drives the electrical energy supply to either energize or de-energize the magnetic field generator; and
an ECG signal generator which signals the controller when there is ventricular diastole and ventricular systole, wherein the controller drives the electrical energy supply to energize the magnetic field generator when the ECG signal generator signals the controller that there is ventricular diastole and wherein the controller drives the electrical energy supply to de-energize the magnetic field generator when the ECG signal generator signals the controller that there is ventricular systole.

6. The artificial ventricle as claimed in claim 1 further including:
an electrical energy supply electrically connected to the magnetic field generator;
a controller which drives the electrical energy supply to either energize or de-energize the magnetic field generator; and
an ECG signal generator which signals the controller when there is ventricular diastole and ventricular systole, wherein the controller drives the electrical energy supply to energize the magnetic field generator when the ECG signal generator signals the controller that there is ventricular diastole and wherein the controller drives the electrical energy supply to de-energize the magnetic field generator when the ECG signal generator signals the controller that there is ventricular systole.

7. A method of left ventricle assist comprising:
removing a portion of the aorta distal of the native aortic valve;
implanting an artificial ventricle to replace the removed portion of the aorta, the artificial ventricle including:
an inlet for receiving blood,
an outlet for discharging blood,
a chamber disposed between the inlet and the outlet, and
an actuation device;
actuating the actuation device, causing the artificial ventricle to expand to an expanded configuration wherein blood flows into the inlet during ventricular systole; and
actuating the actuation device, causing the artificial ventricle to contract to a contracted configuration wherein blood flows out of the outlet during ventricular diastole;
wherein the chamber has a resilient outer wall and the actuation device includes:
a first pad disposed on the resilient outer wall of the chamber, the first pad having a magnetic field generator; and
a second pad disposed on the resilient outer wall of the chamber opposite of the first pad, the second pad having a material which is attracted to the magnetic field generator when the magnetic field generator generates a magnetic field, wherein the second pad moves towards the first pad when the magnetic field generator generates a magnetic field and thereby actuates the artificial ventricle to the contracted configuration by contracting the resilient outer wall of the chamber, and wherein the resilient outer wall of the chamber actuates the artificial ventricle to the expanded configuration when the magnetic field generator is not generating a magnetic field and the material is not attracted to the magnetic field generator.

8. A method of right ventricle assist comprising:
removing a portion of the pulmonary artery distal of the native pulmonic valve;
implanting an artificial ventricle to replace the removed portion of the pulmonary artery, the artificial ventricle including:
an inlet for receiving blood,
an outlet for discharging blood,
a chamber disposed between the inlet and the outlet, and
an actuation device;
actuating the actuation device, causing the artificial ventricle to expand to an expanded configuration wherein blood flows into the inlet during ventricular systole; and
actuating the actuation device, causing the artificial ventricle to contract to a contracted configuration wherein blood flows out of the outlet during ventricular diastole;
wherein the chamber has a resilient outer wall and the actuation device includes:
a first pad disposed on the resilient outer wall of the chamber, the first pad having a magnetic field generator; and
a second pad disposed on the resilient outer wall of the chamber opposite of the first pad, the second pad having a material which is attracted to the magnetic field generator when the magnetic field generator generates a magnetic field, wherein the second pad moves towards the first pad when the magnetic field generator generates a magnetic field and thereby actuates the artificial ventricle to the contracted configuration by contracting the resilient outer wall of the chamber, and wherein the resilient outer wall of the chamber actuates the artificial ventricle to the expanded configuration when the magnetic field generator is not generating a magnetic field and the material is not attracted to the magnetic field generator.

* * * * *